United States Patent
Nelson

(10) Patent No.: US 10,111,656 B2
(45) Date of Patent: Oct. 30, 2018

(54) TISSUE FASTENING SYSTEM AND METHOD

(71) Applicant: Covidien LP, Mansfield, MA (US)

(72) Inventor: Anne Nelson, Guilford, CT (US)

(73) Assignee: Covidien LP, Mansfield, MA (US)

(*) Notice: Subject to any disclaimer, the term of this patent is extended or adjusted under 35 U.S.C. 154(b) by 296 days.

(21) Appl. No.: 15/146,065

(22) Filed: May 4, 2016

(65) Prior Publication Data

US 2016/0331372 A1 Nov. 17, 2016

Related U.S. Application Data

(60) Provisional application No. 62/159,407, filed on May 11, 2015.

(51) Int. Cl.
| | |
|---|---|
| *A61B 17/064* | (2006.01) |
| *A61B 17/068* | (2006.01) |
| *A61B 17/08* | (2006.01) |
| *A61B 17/10* | (2006.01) |

(Continued)

(52) U.S. Cl.
CPC ........ *A61B 17/0643* (2013.01); *A61B 17/068* (2013.01); *A61B 17/0644* (2013.01); *A61B 17/08* (2013.01); *A61B 17/10* (2013.01); *A61B 17/00491* (2013.01); *A61B 17/122* (2013.01);
(Continued)

(58) Field of Classification Search
CPC .......... A61B 17/00491; A61B 17/0643; A61B 17/0644; A61B 17/068; A61B 17/08; A61B 17/10; A61B 17/122; A61B 17/11; A61B 17/1114; A61B 17/115; A61B 17/1152; A61B 2017/00004; A61B 2017/00504; A61B 2017/1103; A61B 2017/1107; A61B 2017/111; A61B 2017/1125; A61B 2017/1132; A61B 2017/1135; A61B 2017/1139

See application file for complete search history.

(56) References Cited

U.S. PATENT DOCUMENTS

| | | |
|---|---|---|
| 4,060,089 A | 11/1977 | Noiles |
| 6,488,196 B1 | 12/2002 | Fenton, Jr. |
| 7,429,266 B2 | 9/2008 | Bonutti et al. |

(Continued)

FOREIGN PATENT DOCUMENTS

EP 1468653 A2 10/2004

OTHER PUBLICATIONS

European Search Report dated Oct. 21, 2016, issued in EP Application No. 16 16 8886.

*Primary Examiner* — Jocelin Tanner

(57) ABSTRACT

A fastening system includes first and second fastening members and a penetrating member. The first fastening member includes a backspan and a set of lobes that extend from the backspan. The second fastening member includes a backspan and a set of lobes that extend from the backspan. The penetrating member includes a first body which is substantially planar, a set of teeth, and a first trailing wall that extends from the first body orthogonal to a plane that is defined by the first body. The set of teeth extend from a leading edge of the first body which is opposite a trailing edge of the first body and are configured to pierce and spread tissue over the set of lobes of the first fastening member. The first trailing wall is configured to support the backspan of the first fastening member.

7 Claims, 5 Drawing Sheets

(51) Int. Cl.
*A61B 17/00* (2006.01)
*A61B 17/122* (2006.01)

(52) U.S. Cl.
CPC ............... *A61B 2017/00004* (2013.01); *A61B 2017/00504* (2013.01)

(56) References Cited

U.S. PATENT DOCUMENTS 8,323,316 B2    12/2012  Maiorino et al.
2016/0296233 A1*  10/2016  Wheeler ............ A61B 17/0643

* cited by examiner

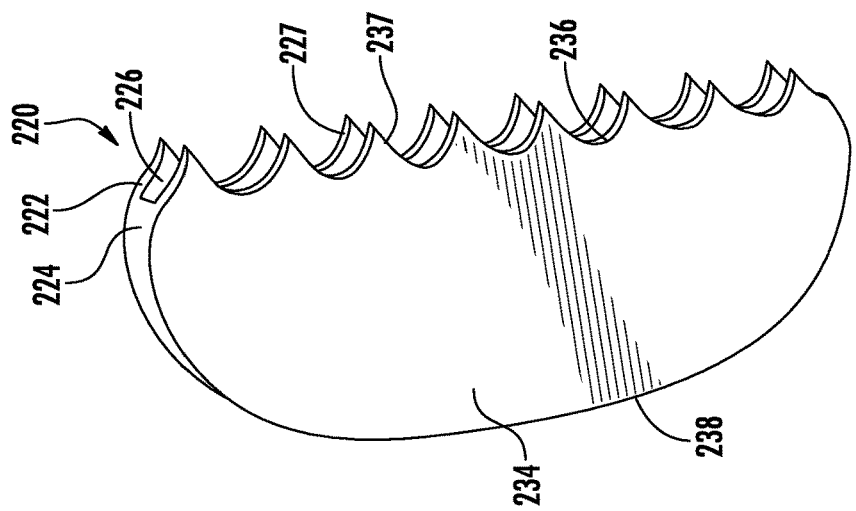
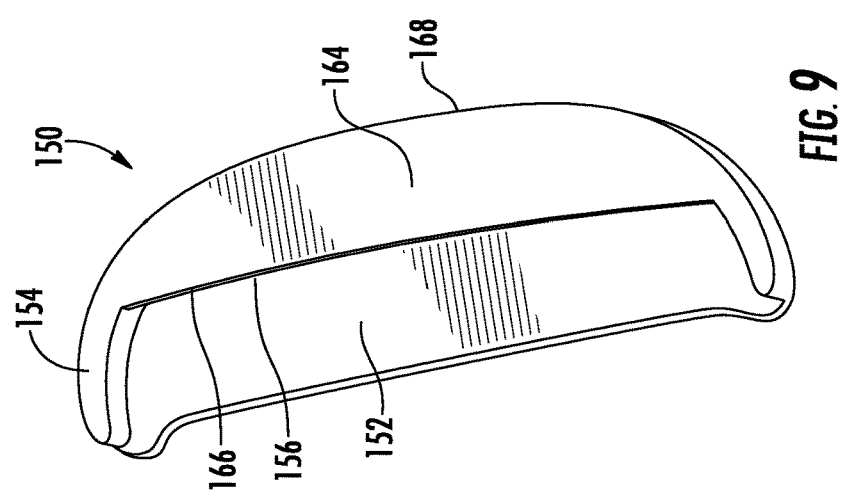
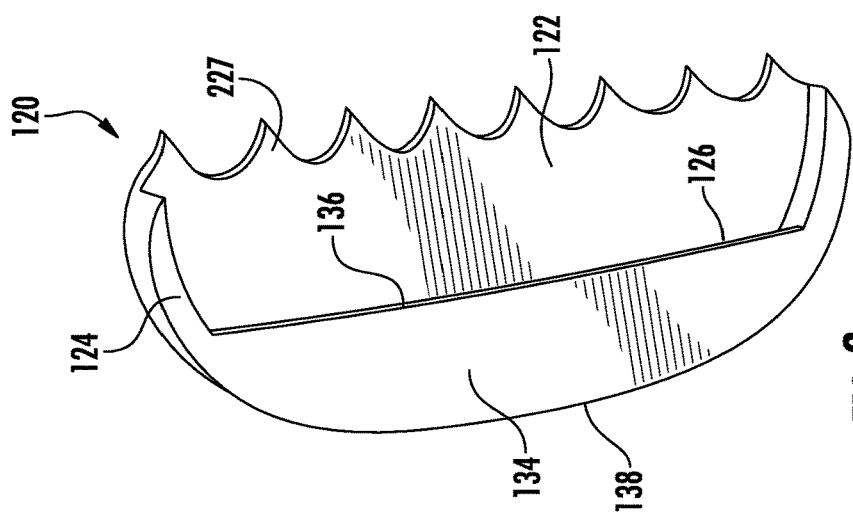

TISSUE FASTENING SYSTEM AND METHOD

CROSS-REFERENCE TO RELATED APPLICATIONS

This application claims the benefit of and priority to U.S. Provisional Patent Application Ser. No. 62/159,407 filed May 11, 2015, the entire disclosure of which is incorporated by reference herein.

BACKGROUND

1. Technical Field

The present disclosure relates to surgical fasteners and, more specifically, to tissue fastening systems having polymeric staples and methods for joining tissue with polymeric staples.

2. Discussion of Related Art

Surgical staples and stapling instruments are well known in the surgical arts and have become an important part of many surgical procedures. The use of stapling instruments for applying staples to join tissue or tissue segments in a fast and efficient manner has obviated the time consuming step of manual suturing of tissue or tissue segments in a variety of surgical procedures, e.g., anastomoses procedures. The reduced time required to perform these surgical procedures using surgical stapling instruments has resulted in reduced trauma and risk to patients.

Usually, surgical staples are made of a metal that is bio-compatible, but not bio-absorbable. The metal staples, therefore, must eventually be removed by another device such as a staple extractor, which is not only time consuming but can cause discomfort and pain to the patient.

Plastic staples can be made bio-absorbable and do not affect medical imaging techniques, such as magnetic resonance imaging, computer tomography scanning, and ultrasound detection. Typically plastic staples are resilient and do not possess the rigidity necessary to penetrate tissue to be joined.

Accordingly, there is a need for stapling systems and methods for joining tissue with plastic staples that penetrate tissue with the plastic staples.

SUMMARY

In an aspect of the present disclosure, a fastening system includes a first fastening member, a second fastening member, and a penetrating member. The first fastening member includes a backspan and a set of lobes that extend from the backspan which are configured to atruamatically pass through tissue. The second fastening member includes a backspan and a set of lobes that extend from the backspan. The penetrating member includes a first body, a set of teeth, and a first trailing wall. The first body is substantially planar. The first trailing wall extends from the first body orthogonal to a plane that is defined by the first body along or adjacent a trailing edge of the first body. The set of teeth extend from a leading edge of the first body which is opposite the trailing edge of the first body and in the plane defined by the first body. The set of teeth are configured to pierce and spread tissue over the set of lobes of the first fastening member. The first trailing wall is configured to support the backspan of the first fastening member.

In aspects, the fastening system includes a backing member that has a second body and a second trailing wall. The second body is substantially planar with the second trailing wall extending from the second body orthogonal to a plane defined by the second body along or adjacent a trailing edge of the second body. The second trailing wall is configured to support the backspan of the second fastening ember. The first and second fastening members may be flexible and the penetrating member and the backing member may be substantially rigid.

In some aspects, the set of lobes of the first fastening member define recesses between each pair of lobes. The set of lobes of the second fastening member may define recesses between each pair of lobes. Each of the recesses of the first fastening member may be configured to receive a respective lobe of the second fastening ember and each of the recesses of the second fastening member may be configured to receive a respective lobe of the first fastening member.

In particular aspects, the set of lobes of the first fastening member define a first tissue contacting surface and the set of lobes of the second fastening member define a seconding tissue contacting surface. The first and second fastening member may be configured to be secured along the first and second tissue contacting surfaces. The first and second fastening members may be configured to be ultrasonically welded together along the first and second tissue contacting surfaces. The first and second fastening members may be bioabsorbable.

In another aspect of the present disclosure, a method of joining tissue includes driving a penetrating member through tissue to be joined, contacting a first tissue contacting surface of a first fastening member with a second tissue contacting surface of a second fastening member, and securing the first and second contacting surfaces along a seam. The first fastening member includes a set of lobes along the first tissue contacting surface. The second tissue contacting surface is shaped to interdigitate with the first tissue contacting surface. Securing the first and second tissue contacting surfaces along the seam which is defined between the first and second tissue contacting surface with tissue to be joined disposed between portion of the first and second tissue contacting surfaces. The first and second fastening members are flexible along the seam when the first and second fastening members are secured together.

In aspects, securing the first tissue contacting surface to the second tissue contacting surface along the seam includes ultrasonically welding the first tissue contacting surface to the second tissue contacting surface along the seam. Ultrasonically welding the first tissue contacting surface to the second tissue contacting surface along the seam includes delivering ultrasonic energy to the penetrating member such that the penetrating member ultrasonically welds the first tissue contacting surface to the second tissue contacting surface along the seam.

In some aspects, driving the penetrating member through the tissue to be joined includes driving a set of teeth that extend from the body through the tissue to be joined. The set of teeth may pierce the tissue to be joined and guide the tissue to be joined over the lobes of the first fastening member. Driving the penetrating member through the tissue to be joined may include each tooth of the set of teeth being aligned with a respective lobe of the set of lobes such that the tooth pierces and then guides the tissue to be joined over the respective lobe.

In particular aspects, driving the penetrating member through the tissue to be joined includes supporting a backspan of the first fastening member with a trailing wall that extends orthogonal to a plane defined by a body of the penetrating member. The trailing wall may engage the backspan of the first fastening member to drive the set of lobes through the tissue to be joined. The method may include positioning the first fastening member on the body of the penetrating member with the backspan of the first fastening member engaged with the trailing wall of the penetrating member before driving the penetrating member through the tissue to be joined.

In certain aspects, contacting the first and second tissue contacting surfaces includes supporting a backspan of the second fastening member with a backing member. Supporting the backspan of the second fastening member may include engaging the backspan of the second fastening member with a trailing wall extending orthogonal to a plane defined by a body of the backing member. The method may include positioning the second fasting member on the body of the backing member with the backspan of the second fastening member engaged with the trailing wall of the backing member before contacting the first tissue contacting surface with the second tissue contacting surface.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 8 is a side view of another penetrating member provided in accordance with the present disclosure;

FIG. 9 is a side view of another backing member provided in accordance with the present disclosure; and FIG. 10 is a side view of another penetrating member provided in accordance with the present disclosure.

DETAILED DESCRIPTION

Figure 1:
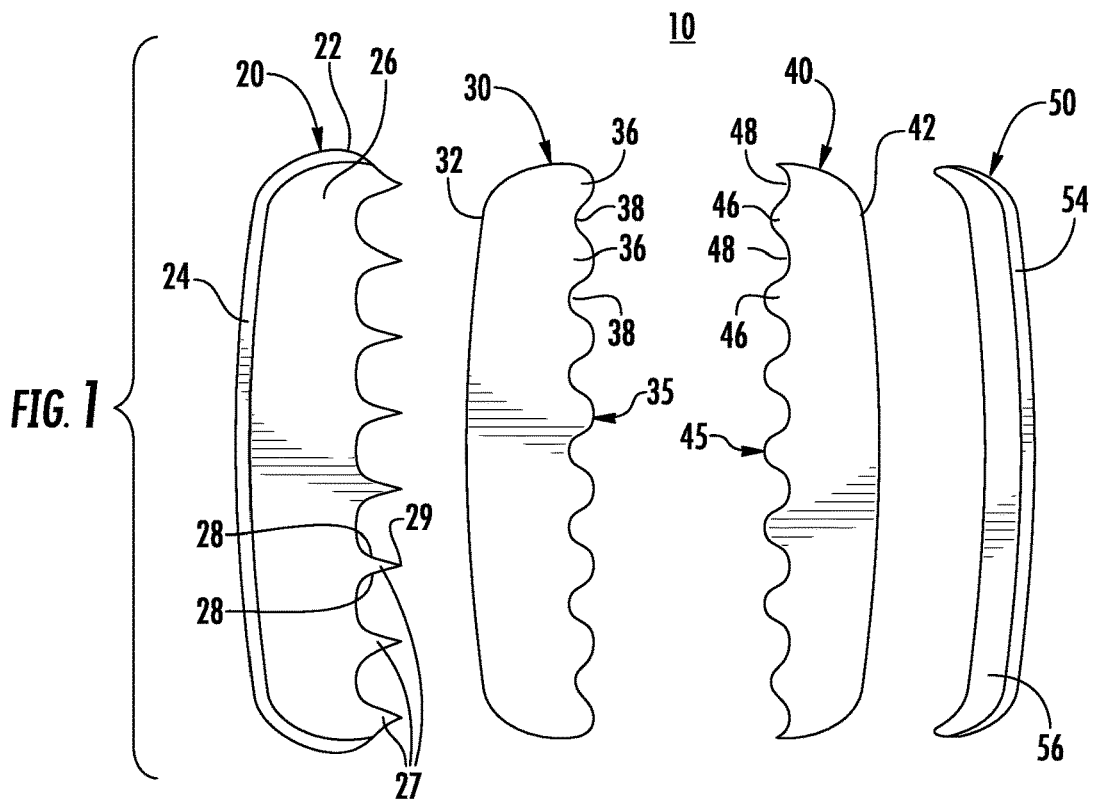
FIG. 1 is a top view of a tissue fastening system provided in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

This disclosure relates generally to a tissue fastening system including a metal penetrating member and a flexible plastic fastener member received by the metal penetrating member. In use, the metal penetrating member pierces tissue and pushes the plastic fastener member through the penetrated tissue. The plastic fastener member is then secured to a plastic retainer to join the penetrated tissue together. The plastic staple may be secured to the plastic retainer by ultrasonic welding. When the penetrated tissue is joined with the plastic fastener member and the plastic retainer, the plastic fastener member and the plastic retainer are flexible enough to allow the penetrated tissue to flex without separating. The plastic fastener member and the plastic retainer may be bioabsorbable such that as the penetrated tissue heals, the plastic fastener member and the plastic retainer are absorbed by the body.

Referring now to FIG. 1, a fastening system 10 for joining tissue with bioabsorbable fastening members 30, 40 is provided in accordance with the present disclosure. The fastening system 10 includes a penetrating member 20, the first fastening member 30, the second fastening member 40, and a backing member 50. The penetrating member 20 and the backing member 50 are substantially rigid and constructed from biocompatible metal or alloy thereof (e.g., surgical steel, titanium, etc.). The first and second fastening members 30, 40 are flexible and constructed from a bioabsorbable material that will be absorbed by the body of a patient after a predetermined amount of time within the body of a patient. Examples of such bioabsorbable materials include, but are not limited to, urethanes blended with lactic acid and/or glycolic acid, homopolymers thereof or copolymers thereof, and acrylates blended with caprolactones such as polycaprolactone dimethacrylate poly(butyl acrylate) blends, and combinations thereof which are disclosed in U.S. Pat. No. 8,323,316, the entire contents of which are hereby incorporated by reference.

Figure 2:
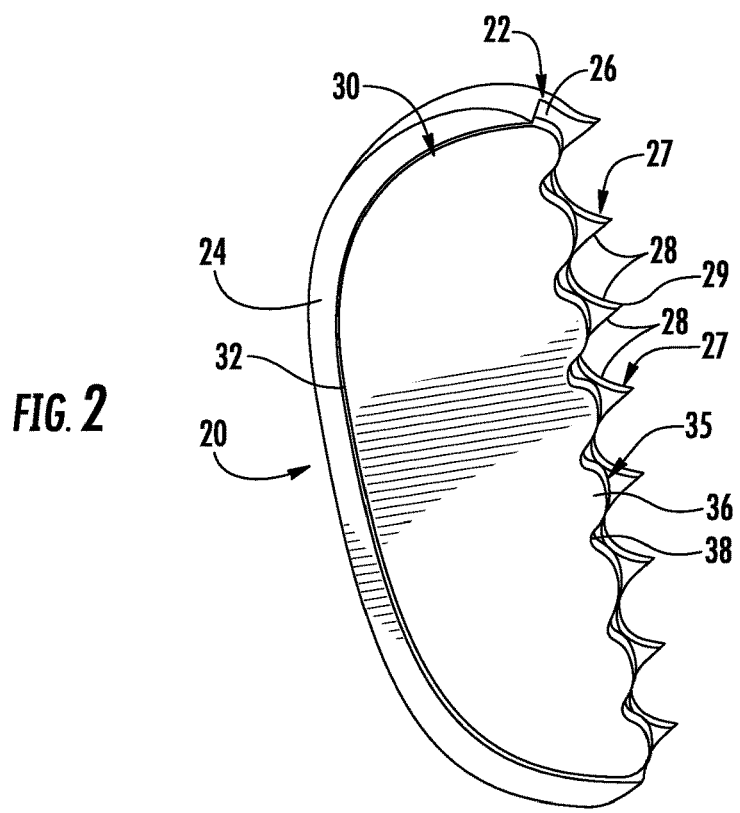
FIG. 2 is a perspective view of the first fastening member of FIG. 1 received in the penetrating member of FIG. 1.
Figure 3:
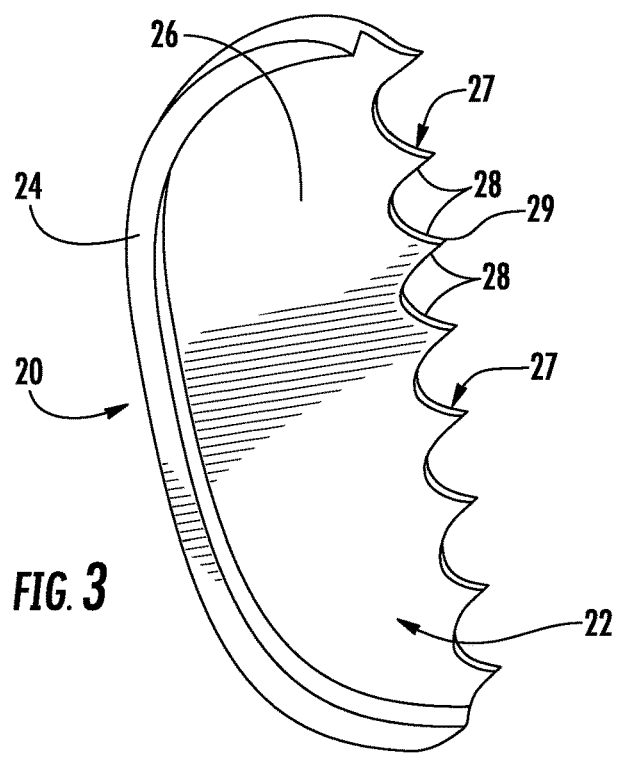
FIG. 3 is a perspective view of the penetrating member of FIG. 1.

With additional reference to FIGS. 2 and 3, the penetrating member 20 has a body portion 22 and an arcuate trailing wall 24. The body portion 22 is substantially planar and defines a shelf 26 on the upper surface thereof. The shelf 26 is configured to receive the first fastening member 30 such that the trailing wall 24 supports a backspan 32 of the first fastening member 30, as detailed below. The leading edge of the body portion 22 includes teeth 27 extending away from the trailing wall 24. The teeth 27 are shaped to penetrate tissue and have sides 28 that intersect at a tip 29. As detailed below, the tip 29 is configured to facilitate penetration of tissue and the sides 28 of the teeth 27 are configured to cut and separate tissue as the first fastening member 30 is driven through tissue.

With particular reference to FIG. 1, each tooth 27 is substantially triangular in shape with substantially linear sides 28. It is contemplated that the sides 28 of each tooth 27 may be arcuate. For example, each of the sides 28 may be concave in profile to decrease the thickness of the tooth 27 or convex in profile to increase the thickness of the tooth 27 when compared to a tooth 27 with substantially linear sides 28. In addition, the sides 28 of each tooth 27 may be concave in profile adjacent the tip 29 and convex in profile adjacent the body portion 22 such that the tooth 27 penetrates and then spreads penetrated tissue. Alternatively, the penetrating member can be configured with a plurality, or one or more, elongate prongs.

With continued reference to FIGS. 1-3, the first and second fastening members 30, 40 each include a backspan 32, 42 and lobes 36, 46. The lobes 36, 46 extend from a respective backspan 32, 42. The lobes 36, 46 form a tissue contacting surface 35, 45 and define a plurality of recesses 38, 48 therebetween. The lobes 36 of the first fastening member 30 are aligned with the recesses 48 of the second fastening member 40 such that the lobes 36 are receivable in the recesses 48 (i.e., the lobes 36 and the recesses 48 interdigitate). Similarly, the lobes 46 of the second fastening member 40 are aligned with the recesses 38 of the first fastening member 30 such that the lobes 46 are receivable in the recesses 38. When the lobes 36, 46 are received in the recesses 38, 48, respectively, the tissue contacting surfaces 35, 45 of the first and second fastening members 30, 40 abut one another to form a seam S (FIG. 5) between the first and second fastening members 30, 40.

The backing member 50 is configured to support the second fastening member 40 and includes a body 52 and a trailing wall 54. The body 52 defines a shelf 56 sized to receive the backspan 42 of the second fastening member 40 as detailed below.

With particular reference to FIG. 2, the first fastening member 30 is sized to be received by the shelf 26 of the penetrating member 20. When the first fastening member 30 is received by the shelf 26 of the penetrating member 20, each lobe 36 of the first fastening member 30 is positioned adjacent one of the teeth 27 of the penetrating member 20. The lobes 36 may be in contact with a respective one of the teeth 27. In addition, when the first fastening member 30 is received by the shelf 26 of the penetrating member 20, each tooth 27 of the penetrating member 20 is aligned with one of the lobes 36 of the first fastening member 30 such that the tip 29 of the tooth 27 extends past the lobe 36. As shown, each tooth 27 substantially bisects each lobe 36; however, it is contemplated that each tooth 27 may be offset from a centerline of each lobe 36. As detailed below, when the penetrating member 20 is driven through tissue, the tips 29 of each tooth 27 pierce tissue and the sides 28 of the teeth 27 separate the tissue such that each lobe 36 passes through an opening made by a respective tooth 27.

Figure 4:
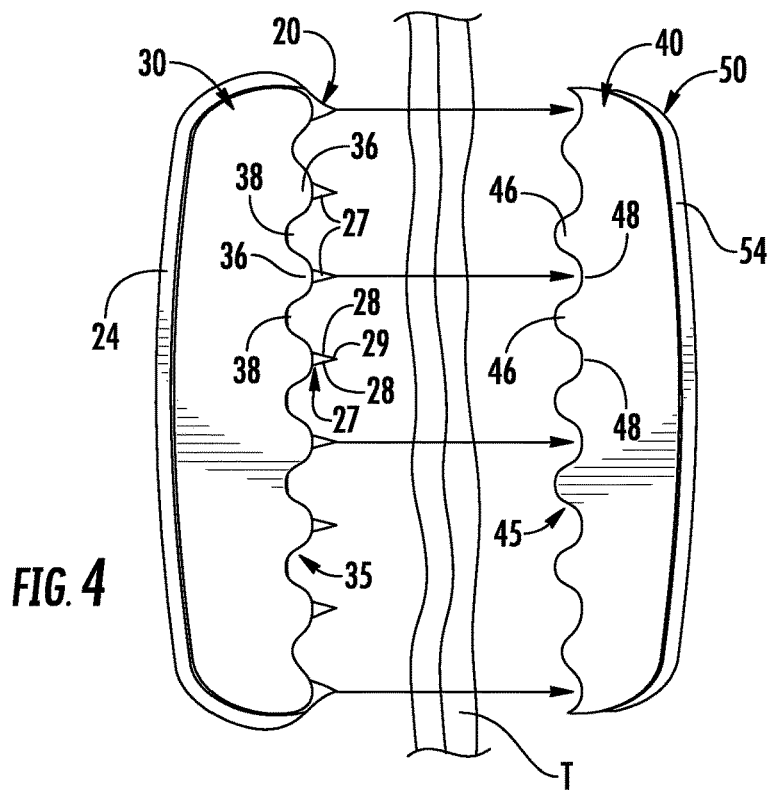
FIG. 4 is a top view of the tissue fastening system of FIG. 1 with tissue positioned between the first and second fastening members.
Figure 5:
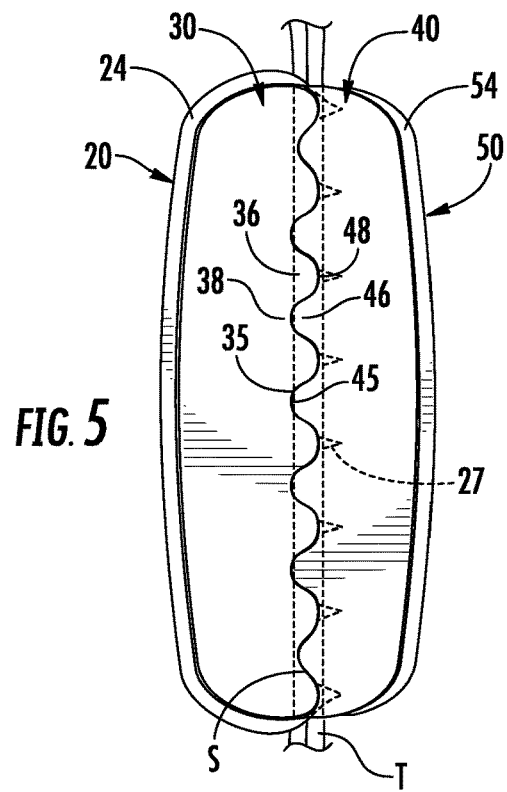
FIG. 5 is a top view of the tissue fastening system of FIG. 4 with the penetrating member driven through tissue and the first and second fastening members in contact with one another.
Figure 6:
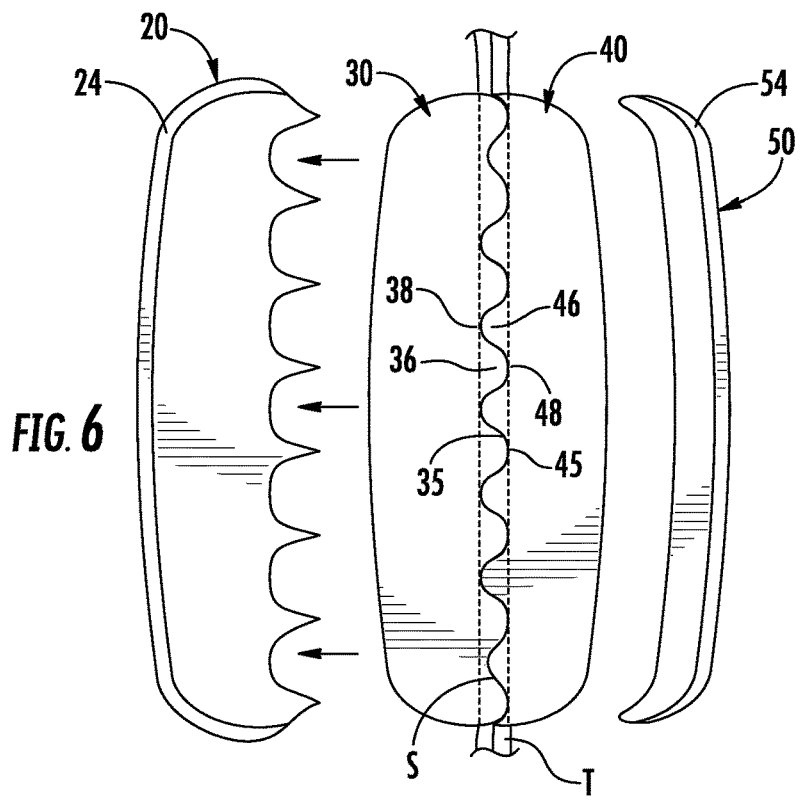
FIG. 6 is a top view of the tissue fastening system of FIG. 5 with the penetrating member and backing member withdrawn from the first and second fastening members respectively.

Referring to FIGS. 4-6, a method for joining tissue is described in accordance with the present disclosure. Initially, the first fastening member 30 is positioned on the body portion 22 of the penetrating member 20 such that the first fastening member 30 is received by the shelf 26 and the second fastening member 40 is positioned on the body portion 52 of the backing member 50 such that the second fastening member 40 is received by the shelf 46 as shown in FIG. 4. Next, the penetrating member 20 is driven through tissue T such that the tips 29 of the teeth 27 of the penetrating member 20 create openings or incisions in the tissue T. As the teeth 27 are driven through the tissue T, the sides 28 of the teeth 27 enlarge the incisions I by spreading the tissue T over the teeth 27. As the incisions are enlarged, the lobes 36 of the first fastening member 30 pass through the enlarged incisions of the tissue T. The second fastening member 40 is positioned on an opposite side of the tissue T from the backspan 32 of the first fastening member 30 and aligned with the first fastening member 30 such that the lobes 36 of the first fastening member 30 are received in recesses 48 of the second fastening member 40 as detailed above. The backing member 50 is positioned against the backspan 42 of the second fastening member 40 to support the backspan 42 as the first fastening member 30 is driven through the tissue T and into contact with the second fastening member 40.

With particular reference to FIG. 5, when the tissue contacting surface 35 of the first fastening member 30 contacts the tissue contacting surface 45 of the second fastening member 40, each tooth 27 of the penetrating member 20 may extend past the tissue contacting surface 45 of the second fastening member 40 adjacent a respective one the recesses 48 of the second fastening member 40. When the tissue contacting surfaces 35, 45 of the first and second fastening members 30, 40 are in contact with one another, the first and second fastening members 30, 40 are joined together along a seam S formed by the tissue contacting surfaces 35, 45. The first and second fastening members 30, 40 may be joined together by welding (e.g., ultrasonically welding) the first and second fastening members 30, 40 together along the seam S. Additionally or alternatively, the first and second fastening members 30, 40 may be joined together by adhesive applied to the tissue contacting surfaces 35, 45. As the first and second fastening members 30, 40 are joined together, the penetrating member 20 and the backing member 50 may be urged towards one another to apply pressure to the tissue contacting surfaces 35, 45 along the seam S.

The ultrasonic energy may be applied to the first and second fastening members 30, 40 by the penetrating member 20. The body portion 22 of the penetrating member 20 may be operatively coupled to a source of ultrasonic energy such that the teeth 27 of the penetrating member 20 deliver ultrasonic energy to the seam to ultrasonically weld the first and second fastening members 30, 40 together along the seam S.

When the first and second fastening members 30, 40 are joined together, the penetrating member 20 is withdrawn from the tissue T and the backing member 50 is removed from the backspan 42 of the second fastening member 40 such that the first and second fastening members 30, 40 remain the joined together with tissue therebetween as shown in FIG. 6. As detailed above, the first and second fastening members 30, 40 are constructed of a bioabsorbable material such that after anastomosis of the joined tissue is completed, the body of the patient absorbs the first fastening member 30 and the second fastening member 40. In addition, the first and second fastening members 30, 40 may be flexible to allow the tissue to flex along the seam while securing the tissue together.

Figure 7:
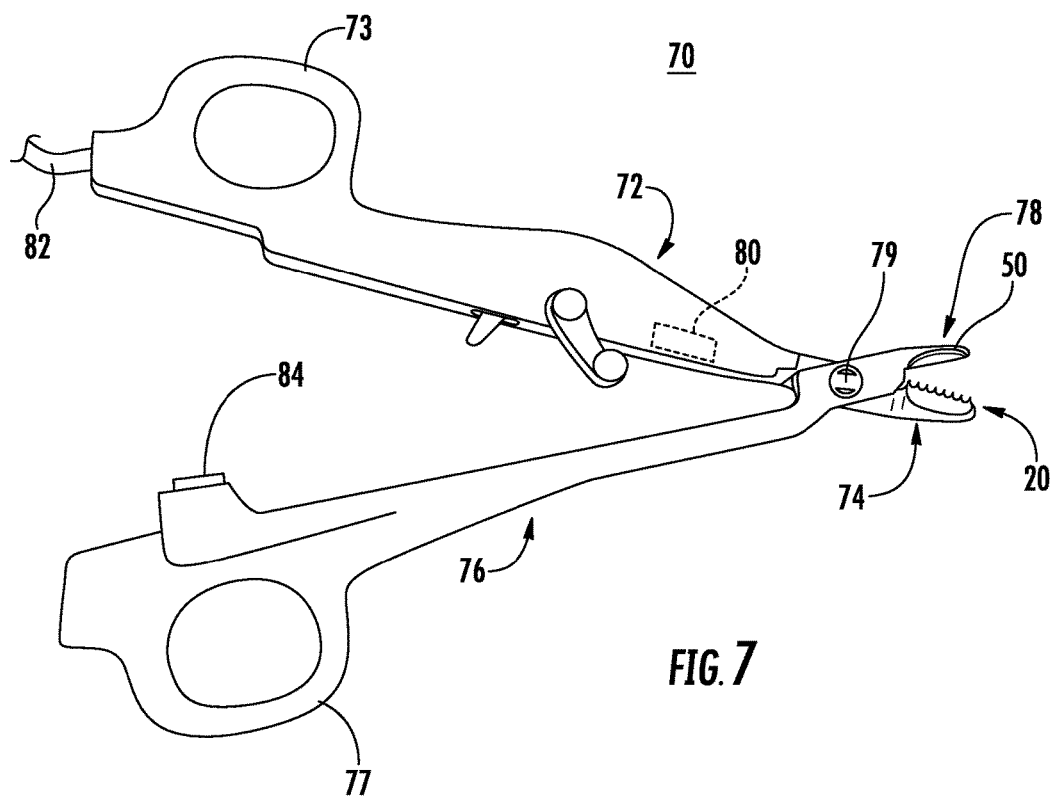
FIG. 7 is a side view of a surgical instrument provided in accordance with the present disclosure including a penetrating member and a backing member.

With reference to FIG. 7, a surgical instrument 70 is provided in accordance with this disclosure and includes a first member 72 and a second member 76 that are pivotally secured to one another. The first and second members 72, 76 each include a handle 73, 77 at a proximal end and a jaw member 74, 78 at the distal end. The first and second member 72, 76 are pivotable about a pivot 79 positioned between the handles 73, 77 and the jaw members 74, 78. The penetrating member 20, as detailed above, is positioned on the jaw member 74 of the first member 72 and the backing member 50 is positioned on the jaw member 78 of the second member 76. When the handles 73, 77 are approximated towards one another, the penetrating member 20 and the backing member 50 are approximated towards one another.

As the handle 73 of the first member 72 is pivoted towards the handle 77 of the second member 76, the jaw member 74 moves the penetrating member 20 towards the backing member 50 supported on the jaw member 78 of the second member 76 which is moving towards the penetrating member 20. As shown, the penetrating member 20 and the backing member 50 are pivoted towards one another; however, it is also contemplated that the surgical instrument may be configured such that the penetrating member 20 and the backing member 50 move towards one another in a parallel manner. When the first and second members 72, 76 are approximated relative to one another, an ultrasonic instrument (not shown) may be used to deliver ultrasonic energy to first and second fastening members (e.g., first and second fastening members 30, 40) disposed in the penetrating member 20 and the backing member 50, respectively.

Alternatively, the first member 72 may be associated with an ultrasonic energy source 80 (e.g., a generator). As shown, the ultrasonic energy source 80 is disposed within the first member 72; however, the ultrasonic energy source 80 may be remote to the surgical instrument 70 and coupled to the first member 72 by a cable 82. The handle 77 of the second member 76 includes an activation switch 84 for selectively delivering ultrasonic energy to the teeth 27 of the penetrating member 20 positioned on the jaw member 74 of the first member 72. When the first and second members 72, 76 are approximated with respect to one another, the activation switch 84 is depressed such that the ultrasonic energy source 80 is activated such that the teeth 27 of the penetrating member 20 weld first and second fastening members 30, 40 received by a shelf 26, 56 of the penetrating member 20 and the backing member 50, respectively, together along a seam S defined between the first and second fastening members 30, 40, as detailed above.

Referring to FIGS. 8-9, another penetrating member 120 and backing member 150 are provided in accordance with the present disclosure. The penetrating member 120 and the backing member 150 are substantially similar to the penetrating member 20 and the backing member 50 detailed above, as such only the differences will be detailed herein for reasons of brevity.

The penetrating member 120 includes a body 122, a trailing wall 124, and an upper plate 134. The trailing wall 124 supports the upper plate 134 substantially parallel to the body 122 such that a shelf or cavity 126 is defined between the upper plate 134 and the body 122. The cavity 126 is configured to receive and support the backspan 34 of the first fastening member 30 in a manner substantially similar to the shelf 26 detailed above with respect to the penetrating member 20. In addition, the trailing wall 124 may support the upper plate 134 slightly askew from the body 122 of the penetrating member 120 with a leading end 136 of the upper plate 134 closer to the body 122 than a trailing end 138 of the upper plate 134. In such embodiments, the leading end 136 may engage the first fastening member 30 to partially secure the first fastening member 30 within the cavity 126.

The backing member 150 includes a body 152, a trailing wall 154, and an upper plate 164. The trailing wall 156 supports the upper plate 164 substantially parallel to the body 152 such that a shelf or cavity 156 is defined between the upper plate 164 and the body 152. The cavity 156 is configured to receive and support the backspan 44 of the second fastening member 40 in a manner substantially similar to the shelf 56 detailed above with respect to the backing member 50. In addition, the trailing wall 154 may support the upper plate 164 slightly askew from the body 152 of the backing member 150 with a leading end 166 of the upper plate 164 closer to the body 152 than a trailing end 168 of the upper plate 164. In such embodiments, the leading end 166 may engage the second fastening member 40 to partially secure the second fastening member 40 within the cavity 166.

Referring now to FIG. 10, another penetrating member 220 is provided in accordance with the present disclosure. The penetrating member 220 is substantially similar to the penetrating member 120 detailed above, as such only the differences will be detailed herein for reasons of brevity.

The penetrating member 220 includes a body 222, a trailing wall 224, and an upper plate 234. The trailing wall 224 supports the upper plate 234 substantially parallel to the body 222 such that a shelf or cavity 226 is defined between the upper plate 234 and the body 222. The upper plate 234 has a leading end 236 having teeth 237 that are substantially aligned in profile with teeth 227 extending from the body 222. The teeth 227, 237 are substantially similar to the teeth 27 detailed above with respect to penetrating member 20 such that when the first fastening member 30 is positioned within the cavity 226, the teeth 227, 237 substantially bisect the lobes 36 of the first fastening member 30 to penetrate and separate tissue over the lobes 36. In addition, the trailing wall 224 may support the upper plate 234 slightly askew from the body 222 of the penetrating member 220 with a leading end 236 of the upper plate 234 closer to the body 222 than a trailing end 238 of the upper plate 234. In such embodiments, the teeth 227 may engage the lobes 38 of the first fastening member 30 to partially secure the first fastening member 30 within the cavity 226.

In addition, the first and second fastening members 30, 40 may be joined together by ultrasonic energy being applied to the first and second fastening members 30, 40 by the teeth 227, 237. The body portion 222 of the penetrating member 220 may be operatively coupled to a source of ultrasonic energy such that the teeth 227, 237 of the penetrating member 220 deliver ultrasonic energy to the seam to ultrasonically weld the first and second fastening members 30, 40 together along the seam S.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A fastening system comprising:
    a first fastening member having a backspan and a set of lobes extending from the backspan configured to atraumatically pass through tissue;
    a second fastening member having a backspan and a set of lobes extending from the backspan; and
    a penetrating member including a first body, a set of teeth, and a first trailing wall, the first body being substantially planar and the first trailing wall extending orthogonal to a plane defined by the first body along a trailing edge of the first body, the set of teeth extending from a leading edge of the first body opposite the trailing edge of the first body and in the plane defined by the first body, the set of teeth configured to pierce and spread tissue over the set of lobes of the first fastening member, the first trailing wall configured to support the backspan of the first fastening member.

2. The fastening system according to claim 1, further comprising a backing member including a second body and a second trailing wall, the second body being substantially planar and the second trailing wall extending orthogonal to a plane defined by the second body along a trailing edge of the second body, the second trailing wall configured to support the backspan of the second fastening member.

3. The fastening system according to claim 1, wherein the first and second fastening members are flexible and the penetrating member is substantially rigid.

4. The fastening system according to claim 1, wherein the set of lobes of the first fastening member define recesses between each pair of lobes, and wherein the set of lobes of the second fastening member define recesses between each pair of lobes, each of the recesses of the first fastening member configured to receive a respective lobe of the second fastening member and each of the recesses of the second fastening member configured to receive a respective lobe of the first fastening member.

5. The fastening system according to claim 1, wherein the set of lobes of the first fastening member defines a first tissue contacting surface and the set of lobes of the second fastening member defines a second tissue contacting surface, the first and second fastening members configured to be secured together along the first and second tissue contacting surfaces.

6. The fastening system according to claim 5, wherein the first and second fastening members are configured to be ultrasonically welded together along the first and second tissue contacting surfaces.

7. The fastening system according to claim 1, wherein the first and second fastening members are bioabsorbable.

* * * * *